US005897541A

United States Patent [19]
Uitenbroek et al.

[11] Patent Number: 5,897,541
[45] Date of Patent: Apr. 27, 1999

[54] LAMINATE MATERIAL AND ABSORBENT GARMENT COMPRISING SAME

[75] Inventors: Duane Girard Uitenbroek, Little Chute; Kathleen Ann O'Rourke, Neenah, both of Wis.

[73] Assignee: Kimberly-Clark Worldwide, Inc., Neenah, Wis.

[21] Appl. No.: 08/807,965

[22] Filed: Feb. 28, 1997

Related U.S. Application Data

[63] Continuation of application No. 08/316,181, Sep. 30, 1994, abandoned.

[51] Int. Cl.$^6$ .................................................. A61F 13/15
[52] U.S. Cl. ........................................ 604/358; 604/385.1
[58] Field of Search ..................................... 604/358, 366, 604/370, 380, 385.1

[56] References Cited

U.S. PATENT DOCUMENTS

| | | |
|---|---|---|
| 3,675,654 | 7/1972 | Baker . |
| 3,952,746 | 4/1976 | Summers . |
| 4,249,532 | 2/1981 | Polansky ............................... 604/385.1 |
| 4,609,584 | 9/1986 | Cutler et al. ............................. 428/156 |
| 4,623,340 | 11/1986 | Luceri .................................. 604/385.1 |
| 4,673,403 | 6/1987 | Lassen et al. ......................... 604/385.1 |
| 4,801,494 | 1/1989 | Datta et al. .............................. 428/283 |
| 5,133,707 | 7/1992 | Rogers et al. ........................... 604/389 |
| 5,192,606 | 3/1993 | Proxmire et al. ........................ 428/284 |
| 5,509,915 | 4/1996 | Hanson et al. ............................ 604/378 |

FOREIGN PATENT DOCUMENTS

| | | |
|---|---|---|
| 0 140 560 A1 | 5/1985 | European Pat. Off. . |
| 1 070 514 | 6/1967 | United Kingdom . |
| 1 265 483 | 3/1972 | United Kingdom . |
| 2255745 | 11/1992 | United Kingdom . |
| WO92/01759 | 2/1992 | WIPO . |

OTHER PUBLICATIONS

ASTM Designation: D 4820 —92a "Standard Test Method for Carbon Black—Surface Area by Multipoint B.E.T. Nitrogen Adsorption", pp. 781–785.

U.S. Patent Application Serial No. 08/096,654 entitled "Thin Absorbent Article Having Rapid Uptake of Liquid," filed Jul. 22, 1993, in the name of Hanson et al.

Journal of American Chemical Society, vol. 60, Feb. 1938 pp. 309–319, "Adsorption of Gases in Multimolecular Layers" by Stephen Brunauer, P. H. Emmett and Edward Teller.

ASTM Designation: D 2244—85 "Standard Method for Calculation of Color Differences From Instrumentally Measured Color Coordinates", pp. 297–301.

*Primary Examiner*—Michael J. Milano

[57] ABSTRACT

Disclosed is a laminated material comprising a first layer of material and a second layer of material. The first layer of material includes opaque areas and transparent areas. The second layer of material has a coloration which is different than the first layer of material and is adjacent the first layer of material so that the coloration of the second layer of material is visible through the transparent areas of the first layer of material. Also disclosed is an absorbent garment including such a laminated material.

40 Claims, 1 Drawing Sheet

LAMINATE MATERIAL AND ABSORBENT GARMENT COMPRISING SAME

This is a continuation of application Ser. No. 08/316,181, filed Sep. 30, 1994, now abandoned.

BACKGROUND OF THE INVENTION

Absorbent garments such as disposable diapers, training pants, adult incontinence products, feminine care products and the like are known. The external surfaces of many such absorbent products comprise a nonwoven fibrous material or a film material. In many instances, it is desirable to have indicia, such as lettering or figures, appear on the exterior surfaces of such products. Unfortunately, it is often difficult to provide such indicia on the materials which typically form the external surfaces (including the outer surface and body contacting surface) of such products.

It has been proposed to print the desired indicia on the films or nonwoven materials which form the external surfaces of such products. Printing on many film and nonwoven surfaces is difficult and often requires additional time and expense in the form of chemical or physical treatments.

It has also been proposed to emboss color-contrasting materials together such that, in the areas of such embossing, color variations are seen. In this manner, indicia can be provided in a manner other than printing.

Nonetheless, it is desirable to provide alternative methods of providing indicia on the external surfaces of absorbent products such as those discussed above. It Is to this goal that the present invention is directed.

SUMMARY OF THE INVENTION

In one aspect, the present invention relates to a laminate material. The laminate material comprises a first layer of material having opaque areas, transparent areas and a coloration. The laminate further comprises a second layer of material adjacent said first layer of material. The second layer of material has a different coloration than said first layer of material, whereby the coloration of said second layer of material is visible through said transparent areas of said first layer of material to a greater extent than through said opaque areas of said first layer of material.

In another aspect, the present invention concerns a disposable absorbent garment. The garment comprises a bodyside liner; an outer cover and an absorbent core located between said bodyside liner and said outer cover. The outer cover comprises a laminate material. The laminate material comprises a first layer of material having opaque areas, transparent areas and a coloration. The laminate further comprises a second layer of material adjacent said first layer of material. The second layer of material has a different coloration than the first layer of material, whereby the coloration of the second layer of material is visible through said transparent areas of said first layer of material to a greater extent than through said opaque areas of said first layer of material.

In a final aspect, the present invention concerns a disposable absorbent garment. The garment comprises a bodyside liner, an outer cover and an absorbent core located between said bodyside liner and said outer cover. The bodyside liner comprises a laminate material. The laminate material comprises a first layer of material having opaque areas, transparent areas and a coloration. The laminate material further comprises a second layer of material adjacent said first layer of material. The second layer of material has a different coloration than said first layer of material, whereby the coloration of the second layer of material is visible through said transparent areas of said first layer of material to a greater extent than through said opaque areas of said first layer of material.

DETAILED DESCRIPTION OF THE PREFERRED EMBODIMENT

Figure 1:
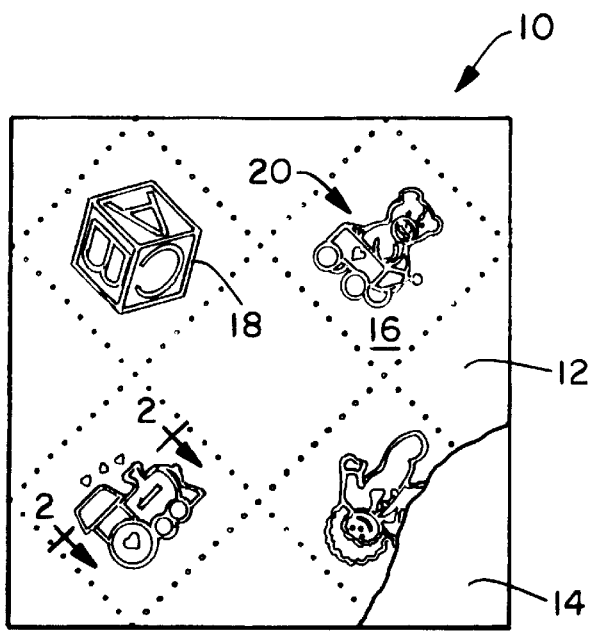
FIG. 1 illustrates a top plan view of a laminate material according to the present invention.

In a first aspect, the present invention relates to a laminate material. The laminate material comprises a first layer of material and a second layer of material. The first layer of material has opaque areas and transparent areas. As used herein, the word "opaque" refers to a material which generally inhibits the passage of light such that written or printed indicia located opposite the opaque material is generally not visible to the naked eye. As a general rule, a material will be considered to be opaque when it has a light transmission of less than or equal to about 80 percent, alternatively of from about 40 to about 70 percent, alternatively of less than about 40 percent. As used herein, the word "transparent" refers to a material through which light readily passes such that written or printed indicia located opposite the transparent material can be viewed by the naked eye. As a general rule, a material will be considered to be transparent when it has a light transmission of greater than about 50 percent, alternatively greater than about 80 or 90 percent, alternatively from about 50 to about 100 percent; and has a light transmission at least 10 percent, alternatively at least 30 percent, alternatively from 20 to 90 percent greater than the light transmission of the opaque areas of the first layer of material.

The light transmission of a material, such as the opaque and transparent areas of the first layer of material, is suitably determined by BYK Gardener as set forth in ASTM-D2244-85.

Any material possessing the described opaque areas and transparent areas is believed suitable for use as the first layer of material in the present invention. The first layer of material is suitably formed from nonwoven materials, woven or knit materials, open or closed cell foam materials, or film materials. The first layer of material may be a single layer of material or may, itself, be a laminate material.

Suitable nonwoven materials include fibrous nonwoven materials formed by a carding process, or a spunbond process, or meltblown process whereby molten polymeric material is extruded through a die, attenuated to lengthen the extruded polymer into fibers and decrease the diameter thereof and is subsequently deposited on a forming surface. Methods of forming such nonwoven materials are known to those skilled in the art. Polymeric materials suitable for use in forming such fibrous nonwoven materials include polyolefins such as polyethylene and propylene, polyesters, nylons, ethylene vinyl acetate, ethylene methacrylate, copolymers of the above materials, block copolymers such as A-B-A block copolymers of styrene and butadiene, and the like. In order to render the fibrous nonwoven material opaque, it is generally desired to provide the nonwoven materials with a relatively high surface area. Such high surface area is suitably accomplished by forming the nonwoven material from fibers having a denier of less than about 2.0 d, alternatively of less than about 1.0 d. The nonwoven materials should suitably have a surface area of at least about 0.3 square meters per gram, alternatively of at least about 0.5 square meters per gram, still further, alternatively of from about 0.6 to about 1.5 square meters per gram. The higher the surface area, the more opaque the nonwoven material will generally appear. The surface area of the fibrous nonwoven materials is suitably determined by the physical gas adsorption (B.E.T.) method of Bruanauer, Emmet, and Teller, *Journal of American Chemical Society*, Vol 60, 1938, p 309, as standardized in ASTM D 4820-92a. The multi-point (5 points), static volumetric method is used with krypton as the adsorption gas and 90° C. as the preliminary drying temperature. The analyses were performed by Micromeritics Instrument Corporation, Norcross, Ga., under their test designation # 260/65000/00 using an automatic DigiSorb 2600 instrument.

As will be explained in greater detail below, the transparent areas present in the first layer of material are generally provided by physical treatment of areas of an opaque first layer of material to render said areas transparent. Accordingly, some known methods of rendering nonwoven and film materials opaque are not suitable for use in the present invention. This is because it is generally not possible to subsequently render such opaque materials transparent.

In one embodiment of the present invention, the fibrous nonwoven materials are rendered opaque due to their high surface area. This allows opaque areas of the nonwoven material to be rendered transparent by application of heat and/or pressure to soften or melt the material forming the nonwoven opaque areas, thus, transforming the fibrous nonwoven material into a filmlike material, which film is transparent. Specifically, the surface area of the nonwoven material is reduced by at least about 25 percent, alternatively by at least about 40 percent, alternatively of from about 50 to about 90 percent based on the surface area of the opaque areas prior to application of heat and/or pressure.

Alternatively, the first layer of material may comprise a film or open or closed cell foam material Suitable film or foam materials are cast or extruded films or foams formed from polyolefins such as polyethylene and propylene, polyesters, nylons, ethylene vinyl acetate, ethylene methacrylate, copolymers of the above materials, block copolymers such as A-B-A block copolymers of styrene and butadiene, and the like. Again, the films and foams suitable for use in the present invention should have a generally opaque character and should be capable of being rendered transparent through the application of heat, pressure, or the like. Thus, the films and foams cannot generally be rendered opaque through certain known means such as by incorporating in such films coloring agents or pigments.

Methods of providing film material with a high surface area include embossing, creating micropores, and the like. One method for creating micropores in films includes adding a noncompatible particulate material to the polymeric material from which the film is to be made, making the film and stretching the film to eliminate or reduce the bond between the polymeric material from which the film is made and the particulate material.

It is particularly desired that the film or foam material suitable for use as the first layer of material have a surface area of at least about 0.3 square meters per gram, alternatively of at least about 0.5 square meters per gram, and more particularly of from about 0.6 to about 1.5 square meters per gram. The surface area of a film is suitably determined by physical gas adsorption (B.E.T.) described above.

The first layer of material suitably has a basis weight of from about 5.0 grams per square meter to about 100 grams per square meter, alternatively of from about 10 to about 50 grams per square meter, more particularly of from about 14 to about 30 grams per square meter. Naturally, the degree of opacity of the first layer of material will be affected, to some degree, by the thickness of the first layer. Thus, obtaining the desired degree of opacity can be achieved by controlling the surface area and thickness of the first layer of material.

The first layer of material is treated to provide it with transparent areas having a basis weight greater than 0 grams per square meter. As discussed above, such treatment generally consists of applying thermal energy through a discontinuous heat bonding, sonic bonding, or pressure embossing operation. The application of thermal energy causes the material from which the first layer of material is formed to soften or melt. This allows certain areas of the first layer of material to be formed into areas which are transparent. This application of thermal energy reduces the surface area of the areas so treated and, thus, renders them less opaque.

Other methods of providing a first layer of opaque material with transparent areas may be apparent to those skilled in the art. For example, it may be possible to provide the first layer with an opaque nature through the addition of a thermally or pressure sensitive pigment such that subsequent application of heat or pressure transforms the pigment into a transparent form, thus, allowing for the formation of transparent areas. Of course, the reverse is also possible. The thermally or pressure sensitive pigment could become opaque upon application of heat or pressure, thus, allowing for the formation of opaque areas.

The laminate material of the present invention further comprises a second layer of material adjacent said first layer of material. As used herein, the second layer of material will be considered to be adjacent the first layer of material when the second layer of material can be viewed through the transparent areas of the first layer of material. Generally, the first and second layers of material will be in an overlapping superimposed relationship. Nonetheless, it may be possible to interpose various layers of material between the first layer of material and the second layer of material.

The second layer of material has a different coloration than the first layer of material. That is, the colors of the first and second layers of material are contrasting such that when the second layer of material is viewed through the transparent areas of the first layer of material, the pattern of transparent areas is readily apparent. Typically, the second layer of material will be of a darker coloration than the first layer of material. In one specific embodiment, the first layer of material has a white coloration in the opaque areas and is colorless in the transparent areas. The second layer of material has a color other than white such that the coloration of the second material can be viewed through the transparent areas of the first layer of material to a greater extent than through the opaque areas of the first layer of material. In a preferred embodiment, the second layer of material can be viewed through the transparent areas of the first layer of material and not through the opaque areas of the first layer of material. The second layer of material may, for example, be a blue color.

The second layer of material may be formed from any material capable of having a coloration different than the first layer of material and of being placed in an adjacent relationship with said first layer of material. The second layer of material suitably comprises a paper or tissue layer, a film, a woven material, a nonwoven material (such as a layer of pulp fibers), or the like. The coloration of the second layer of material can be controlled by any means known to those skilled in the art. Suitably, the second layer will be provided with a coloration through the addition of pigments, dyes, fillers, printing, or the like. Of course, the first and second layers could be of materials which have natural colorations which differ.

It is also possible for the second layer of material to have multiple colorations. That is, the second layer of material may, for example, be printed so as to be one color in a first area and a second color in a second area. The second layer of material may also contain printing or drawings or figures such that its coloration varies across its surface.

Any method of bringing the first and second layers into an adjacent relationship is suitable for use in the present invention. The first and second layers may be laid one on top of the other without being directly attached to one another across the majority of their surface. Alternatively, the first and second layers may be generally attached to one another across their entire surface. Alternatively, the first and second layers may be intermittently attached to each other across their surface or may be attached to one another at their peripheries. Further, the first and second layers may be attached to one another at the same time the transparent areas are formed in the first layer, such as when the transparent areas are formed through a process involving the application of heat and/or pressure. That is, the first and second layers of material may be thermally laminated together.

In a specific embodiment, the transparent areas are formed in the first layer of material in a process separate from that used to bring the second layer of material into an adjacent relationship with said first layer of material. Thus, it is generally preferred that the first layer of material and second layer of material not be co-embossed. Further, in an alternative specific embodiment, the first and second layers of material are not adhesively attached to one another across their entire surfaces. If the first and second layers are adhered together, it may be desired that the adhesive pattern used to Join the two layers together not directly coincide with the transparent areas of said first layer of material. That is, when the first and second layers are adhesively attached, the adhesive is suitably randomly applied between the two layers of material in a manner which does not correspond to the transparent areas of the first layer of material. It is generally desired that the adhesive be colorless so as to not be visible through the transparent areas of the first layer of material. Thus, the adhesive does not unacceptably interfere with viewing the second layer of material through the transparent areas of said first layer of material. It may be possible for the adhesive to comprise the second layer.

The present invention can be further understood from reference to the drawings wherein FIG. 1 Illustrates a laminate material according to the present invention. The laminate material 10 comprises a first layer of material 12 and a second layer of material 14 adjacent and in an overlapping relationship with said first layer of material. The first layer of material 12 includes opaque areas 16 and transparent areas 18. In the illustrated embodiment, the transparent areas correspond to the figures which are visible on the laminate.

Figure 2:
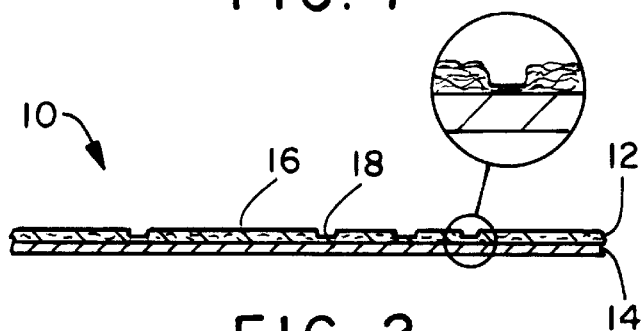
FIG. 2 illustrates a cross-sectional view of the laminate illustrated in FIG. 1 taken along line 2—2 of FIG. 1.

This aspect of the present invention can best be understood by reference to FIG. 2 which is a cross-sectional view taken along line 2—2 of FIG. 1. As can be seen from reference to FIG. 2, the first layer of material comprises a nonwoven material having opaque areas 16. The transparent areas 18 have been formed by application of thermal energy to melt the material from which the first layer 12 is formed to form filmlike areas which are transparent. The second layer of material 14 can then be viewed through the transparent areas 18 such that the FIGS. 20 (FIG. 1) are visible on the surface of the laminate material.

The laminate materials of the present invention are suitable for use in the formation of disposable absorbent garment such as infant diapers, training pants, adult incontinence products, feminine care products, and the like. The laminates are also suitable for use in forming disposable articles such as hospital drapes and gowns, and the like. When used in the formation of disposable absorbent garments, the laminate materials of the present invention suitably form the external surface of the garment. The external surface of the garment may comprise the outer surface of the garment, when the garment is in use, or may comprise the interior surface of the garment when the garment is in use. Thus, the laminate materials of the present invention may, for example, form an inner bodyside liner or an outer liquid-impervious exterior surface.

It is generally desired that the outer surface of an absorbent garment (when in use) be liquid impermeable. Accordingly, in one embodiment of the present invention, the first layer of material comprises a fibrous nonwoven material and the second layer of material comprises a liquid-impervious film. Alternatively, the outer surface of an absorbent garment could be formed from a film/film laminate. When the laminate materials of the present invention are used for the interior surface of absorbent garments, it is generally preferred that the materials be liquid pervious. In this embodiment, the first layer of material may again comprise a fibrous nonwoven material which has been treated to be generally hydrophilic and, thus, liquid pervious, and the second layer of material comprises another liquid-pervious material such as a nonwoven material or a tissue.

Figure 3:
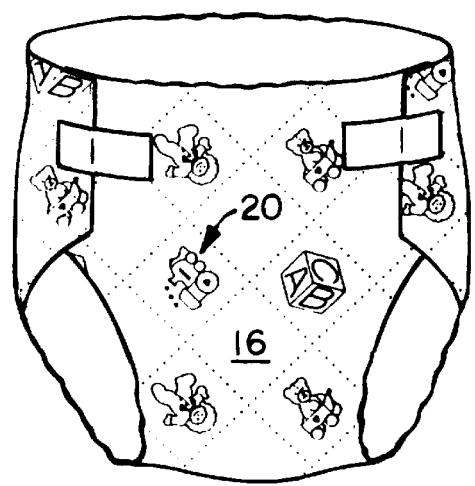
FIG. 3 illustrates the laminate illustrated in FIG. 1 in position on a disposable Infant diaper.

FIG. 3 illustrates the laminate materials of the present invention in place as the outer surface of a disposable infant diaper.

When the laminate materials of the present invention are used as illustrated in FIG. 3, as the exterior surface of an absorbent garment, the transparent areas may also serve as a wetness indicator whereby a caretaker is allowed to determine when the garment has become soiled. That is, the transparent areas of the first layer of material may allow a caretaker to visualize a color change indicating that the garment has been used. Disposable absorbent garments, on which the laminate materials of the present invention may be used, are well known in the art. Suitable disposable garments are disclosed, for example, in commonly assigned U.S. patent application Ser. No. 08/096,654 entitled, "Thin Absorbent Article Having Rapid Uptake of Liquid," filed Jul. 22, 1993, in the name of Hanson, et al. now U.S. Pat. No. 5,509,915; and U.S. Pat. No. 5,192,606 issued Mar. 9, 1993, to Proxmire et al.

EXAMPLES

Example 1

A first layer of material is provided. The first layer of material comprises a 1.2 mil (0.03 millimeter) microporous, white polypropylene film having a basis weight of 29 grams per square meter, which film is commercially available from the 3M Company under the trade designation XKO-8044. The microporous film has a light transmission of 43 percent. The microporous film is passed through a heated embossing nip heated to about 235 degrees Fahrenheit (112° C.) at a pressure of about 150 pounds per linear inch (1034 Kilopascals) to form transparent areas corresponding to the embossing pattern. The transparent areas have a light transmission of 80–90 percent. The first layer of material is then placed adjacent a second layer of material comprising a blue pigmented tissue having a basis weight of bout 10 grams per square meter.

Example 2

A first layer of material comprising a laminate is formed. The laminate is formed from the microporous film used in Example 1 and a 0.5–0.7 ounce per square yard (17–24 grams per square meter) polypropylene spunbond material. The laminate is formed by passing the microporous film and the spunbond material through an embossing nip in which the patterned roll contacts the spunbond material and the anvil roll contacts the film material. The temperature of the pattern roll is 290–300 degrees Fahrenheit (143–149° C.) and the temperature of the anvil roll is 210–250 degrees Fahrenheit (99–121° C.). The nip pressure is about 150 pounds per linear inch (1034 Kilopascals). Transparent areas corresponding to the embossing pattern are thus formed. The laminate thus formed serves as the first layer which is placed adjacent a 0.6 mil (0.015 millimeter) 14 grams per square meter, blue pigmented, polypropylene film commercially available from Edison Plastics, South Plainfield, N.J. 07080, under the trade designation XP-500 (Blue).

Example 3

A first layer of material is provided. The first layer of material comprises a polypropylene microfiber (fiber denier less than about 1.0 d) meltblown material. The first layer has a basis weight of 10, 20 or 40 grams per square meter (gsm). The light transmission of the 10 gsm material is 77 percent, of the 20 gsm material is 55 percent, and of the 40 gsm material is 35 percent. These materials are passed through an embossing nip having a temperature of from about 230 degrees Fahrenheit (110° C.) to about 270 degrees Fahrenheit (132° C.) at a pressure of about 150 pounds per linear inch (1034 Kilopascals). Transparent areas corresponding to the embossing pattern are thus formed. The transparent areas have a light transmission of about 85 to 90 percent. These material are then placed adjacent to a second layer of contrasting color such as the pigmented tissue layer of Example 1.

Example 4

The microfiber meltblown layers of Example 3 are used in forming laminates which form the first layer of material. The microfiber meltblown layers of Example 3 are laminated to the 0.5 to 0.7 ounce per square yard (17–24 gsm) polypropylene spunbond material of Example 2 under the conditions set forth in Example 2. The laminated material thus formed comprises the first layer of material which is then placed adjacent a second layer of material having a contrasting color.

Example 5

A first layer of material is provided. The first layer of material comprises a spunbond material formed from polypropylene fibers having a denier of 1.2 d. The first layer of material has a basis weight of 24 grams per square meter or 48 grams per square meter. The 24 grams per square meter material has a light transmission of 77 percent and the 48 grams per square meter material has a light transmission of 65 percent. Each of the two spunbond materials are then passed through an embossing nip having a temperature of 335 to 350 degrees Fahrenheit (168–171° C.) and a pressure of 200 pounds per linear inch (1379 Kilopascals). Transparent areas corresponding to the embossing pattern are thus formed. The transparent areas have a light transmission of 80 to 87 percent. The first layers of material thus formed are placed adjacent a second layer of contrasting color. Those materials comprising nonwoven webs placed adjacent a tissue layer could be used as bodyside liners, while those materials comprising or placed adjacent a film material could be used as outer covers in absorbent garments.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A laminate material, the laminate material comprising:
   a first layer of nonwoven fibrous material, the material having fibrous opaque areas, filmlike transparent areas and a coloration,
   the first layer having a basis weight of from about 5.0 to about 100 grams per square meter and being formed from fibrous material having a denier of less than about 2.0 d,
   wherein the opaque areas have surface areas of at least 0.3 square meters per gram and light transmissions of not more than about 40 percent,
   wherein the transparent areas have low surface areas relative to the opaque areas, and have been formed by application of a temperature of at least 230° F. to portions of the nonwoven material to reduce the surface area of the portions of nonwoven material by at least 25 percent, based on the surface area of the opaque areas prior to the application of thermal energy, to less than about 0.225 square meters per gram, and
   wherein the transparent areas have light transmissions of greater than 80 percent; and
   a second layer of material adjacent and bonded to the first layer of material, the second layer of material having a different coloration than the first layer of material,
   whereby the coloration of the second layer of material is visible through the transparent areas of the first layer of material to a greater extent than through the opaque areas of the first layer of material.

2. The laminate material according to claim 1, wherein the transparent areas have been formed by application of a temperature of at least 230° F. to portions of the nonwoven material to reduce the surface area of the portions of nonwoven material by at least 40 percent, based on the surface area of the opaque areas prior to the application of thermal energy, to less than about 0.18 square meters per gram.

3. The laminate material according to claim 1, wherein the transparent areas have been formed by application of a temperature of at least 230° F. to portions of the nonwoven material to reduce the surface area of the portions of nonwoven material by at least 50 percent, based on the surface area of the opaque areas prior to the application of thermal energy, to less than about 0.15 square meters per gram.

4. The laminate material according to claim 1, wherein the opaque areas have surface areas of at least 0.5 square meters per gram, and the transparent areas have been formed by application of a temperature of at least 230° F. to portions of the nonwoven material to reduce the surface area of the portions of nonwoven material by at least 25 percent, based on the surface area of the opaque areas prior to the application of thermal energy, to less than about 0.375 square meters per gram.

5. The laminate material according to claim 1, wherein the transparent areas have been formed by application of a temperature of at least 230° F. to portions of the nonwoven material to reduce the surface area of the portions of nonwoven material by at least 40 percent, based on the surface area of the opaque areas prior to the application of thermal energy, to less than about 0.3 square meters per gram.

6. The laminate material according to claim 1, wherein the transparent areas have been formed by application of a temperature of at least 230° F. to portions of the nonwoven material to reduce the surface area of the portions of nonwoven material by at least 50 percent, based on the surface area of the opaque areas prior to the application of thermal energy, to less than about 0.25 square meters per gram.

7. The laminate material according to claim 1, wherein the opaque areas have surface areas of from about 0.6 to about 1.5 meters per gram, and the transparent areas have been formed by application of a temperature of at least 230° F. to portions of the nonwoven material to reduce the surface area of the portions of nonwoven material by at least 25 percent, based on the surface area of the opaque areas prior to the application of thermal energy, to less than about 1.125 square meters per gram.

8. The laminate material according to claim 1, wherein the transparent areas have been formed by application of a temperature of at least 230° F. to portions of the nonwoven material to reduce the surface area of the portions of nonwoven material by at least 40 percent, based on the surface area of the opaque areas prior to the application of thermal energy, to less than about 0.9 square meters per gram.

9. The laminate material according to claim 1, wherein the transparent areas have been formed by application of a temperature of at least 230° F. to portions of the nonwoven material to reduce the surface area of the portions of nonwoven material by at least 50 percent, based on the surface area of the opaque areas prior to the application of thermal energy, to less than about 0.75 square meters per gram.

10. A laminate material, the laminate material comprising:
    a first layer of nonwoven fibrous material, the material having fibrous opaque areas, filmlike transparent areas and a coloration,
        the first layer having a basis weight of from about 5.0 to about 100 grams per square meter and being formed from fibrous material having a denier of less than about 2.0 d,
    wherein the opaque areas have surface areas of at least 0.3 square meters per gram and light transmissions of from about 40 percent to about 70 percent,
    wherein the transparent areas have low surface areas relative to the opaque areas, and have been formed by application of a temperature of at least 230° F. to portions of the nonwoven material to reduce the surface area of the portions of nonwoven material by at least 25 percent, based on the surface area of the opaque areas prior to the application of thermal energy, to less than about 0.225 square meters per gram, and
    wherein the transparent areas have light transmissions of greater than 90 percent; and
    a second layer of material adjacent and bonded to the first layer of material, the second layer of material having a different coloration than the first layer of material,
    whereby the coloration of the second layer of material is visible through the transparent areas of the first layer of material to a greater extent than through the opaque areas of the first layer of material.

11. The laminate material according to claim 10, wherein the transparent areas have been formed by application of a temperature of at least 230° F. to portions of the nonwoven material to reduce the surface area of the portions of nonwoven material by at least 40 percent, based on the surface area of the opaque areas prior to the application of thermal energy, to less than about 0.18 square meters per gram.

12. The laminate material according to claim 10, wherein the transparent areas have been formed by application of a temperature of at least 230° F. to portions of the nonwoven material to reduce the surface area of the portions of nonwoven material by at least 50 percent, based on the surface area of the opaque areas prior to the application of thermal energy, to less than about 0.15 square meters per gram.

13. The laminate material according to claim 10, wherein the opaque areas have surface areas of at least 0.5 square meters per gram, and the transparent areas have been formed by application of a temperature of at least 230° F. to portions of the nonwoven material to reduce the surface area of the portions of nonwoven material by at least 25 percent, based on the surface area of the opaque areas prior to the application of thermal energy, to less than about 0.375 square meters per gram.

14. The laminate material according to claim 10, wherein the transparent areas have been formed by application of a temperature of at least 230° F. to portions of the nonwoven material to reduce the surface area of the portions of nonwoven material by at least 40 percent, based on the surface area of the opaque areas prior to the application of thermal energy, to less than about 0.3 square meters per gram.

15. The laminate material according to claim 10, wherein the transparent areas have been formed by application of a temperature of at least 230° F. to portions of the nonwoven material to reduce the surface area of the portions of nonwoven material by at least 50 percent, based on the surface area of the opaque areas prior to the application of thermal energy, to less than about 0.25 square meters per gram.

16. The laminate material according to claim 10, wherein the opaque areas have surface areas of from about 0.6 to about 1.5 meters per gram, and the transparent areas have been formed by application of a temperature of at least 230° F. to portions of the nonwoven material to reduce the surface area of the portions of nonwoven material by at least 25 percent, based on the surface area of the opaque areas prior to the application of thermal energy, to less than about 1.125 square meters per gram.

17. The laminate material according to claim 10, wherein the transparent areas have been formed by application of a temperature of at least 230° F. to portions of the nonwoven material to reduce the surface area of the portions of nonwoven material by at least 40 percent, based on the surface area of the opaque areas prior to the application of thermal energy, to less than about 0.9 square meters per gram.

18. The laminate material according to claim 10, wherein the transparent areas have been formed by application of a temperature of at least 230° F. to portions of the nonwoven material to reduce the surface area of the portions of nonwoven material by at least 50 percent, based on the surface area of the opaque areas prior to the application of thermal energy, to less than about 0.75 square meters per gram.

19. A laminate material, the laminate material comprising:
a first layer of open or closed cell foam material or film material, the material having opaque areas, transparent areas and a coloration,
the first layer having a basis weight of from about 5.0 to about 100 grams per square meter,
wherein the opaque areas have surface areas of at least 0.3 square meters per gram and light transmissions of not more than about 40 percent,
wherein the transparent areas have low surface areas relative to the opaque areas, and have been formed by application of a temperature of at least 235° F. to portions of the foam material or film material to reduce the surface area of the portions of foam material or film material by at least 25 percent, based on the surface area of the opaque areas prior to the application of thermal energy, to less than about 0.225 square meters per gram, and
wherein the transparent areas have light transmissions of greater than 80 percent; and
a second layer of material adjacent and bonded to the first layer of material, the second layer of material having a different coloration than the first layer of material,
whereby the coloration of the second layer of material is visible through the transparent areas of the first layer of material to a greater extent than through the opaque areas of the first layer of material.

20. The laminate material according to claim 19, wherein the transparent areas have been formed by application of a temperature of at least 235° F. to portions of the foam material or film material to reduce the surface area of the portions of foam material or film material by at least 40 percent, based on the surface area of the opaque areas prior to the application of thermal energy, to less than about 0.18 square meters per gram.

21. The laminate material according to claim 19, wherein the transparent areas have been formed by application of a temperature of at least 235° F. to portions of the foam material or film material to reduce the surface area of the portions of foam material or film material by at least 50 percent, based on the surface area of the opaque areas prior to the application of thermal energy, to less than about 0.15 square meters per gram.

22. The laminate material according to claim 19, wherein the opaque areas have surface areas of at least 0.5 square meters per gram, and the transparent areas have been formed by application of a temperature of at least 235° F. to portions of the foam material or film material to reduce the surface area of the portions of foam material or film material by at least 25 percent, based on the surface area of the opaque areas prior to the application of thermal energy, to less than about 0.375 square meters per gram.

23. The laminate material according to claim 19, wherein the transparent areas have been formed by application of a temperature of at least 235° F. to portions of the foam material or film material to reduce the surface area of the portions of foam material or film material by at least 40 percent, based on the surface area of the opaque areas prior to the application of thermal energy, to less than about 0.3 square meters per gram.

24. The laminate material according to claim 19, wherein the transparent areas have been formed by application of a temperature of at least 235° F. to portions of the foam material or film material to reduce the surface area of the portions of foam material or film material by at least 50 percent, based on the surface area of the opaque areas prior to the application of thermal energy, to less than about 0.25 square meters per gram.

25. The laminate material according to claim 19, wherein the opaque areas have surface areas of from about 0.6 to about 1.5 meters per gram, and the transparent areas have been formed by application of a temperature of at least 235° F. to portions of the foam material or film material to reduce the surface area of the portions of foam material or film material by at least 25 percent, based on the surface area of the opaque areas prior to the application of thermal energy, to less than about 1.125 square meters per gram.

26. The laminate material according to claim 19, wherein the transparent areas have been formed by application of a temperature of at least 235° F. to portions of the foam material or film material to reduce the surface area of the portions of foam material or film material by at least 40 percent, based on the surface area of the opaque areas prior to the application of thermal energy, to less than about 0.9 square meters per gram.

27. The laminate material according to claim 19, wherein the transparent areas have been formed by application of a temperature of at least 235° F. to portions of the foam material or film material to reduce the surface area of the portions of foam material or film material by at least 50 percent, based on the surface area of the opaque areas prior to the application of thermal energy, to less than about 0.75 square meters per gram.

28. A laminate material, the laminate material comprising:
a first layer of open or closed foam material or film material, the material having opaque areas, transparent areas and a coloration,
the first layer having a basis weight of from about 5.0 to about 100 grams per square meter,
wherein the opaque areas have surface areas of at least 0.3 square meters per gram and light transmissions of from about 40 percent to about 70 percent,
wherein the transparent areas have low surface areas relative to the opaque areas, and have been formed by application of a temperature of at least 235° F. to portions of the foam material or film material to reduce the surface area of the portions of foam material or film material by at least 25 percent, based on the surface area of the opaque areas prior to the application of thermal energy, to less than about 0.225 square meters per gram, and
wherein the transparent areas have light transmissions of greater than 90 percent; and
a second layer of material adjacent and bonded to the first layer of material, the second layer of material having a different coloration than the first layer of material,
whereby the coloration of the second layer of material is visible through the transparent areas of the first layer of material to a greater extent than through the opaque areas of the first layer of material.

29. The laminate material according to claim 28, wherein the transparent areas have been formed by application of a temperature of at least 235° F. to portions of the foam material or film material to reduce the surface area of the portions of foam material or film material by at least 40 percent, based on the surface area of the opaque areas prior to the application of thermal energy, to less than about 0.18 square meters per gram.

30. The laminate material according to claim 28, wherein the transparent areas have been formed by application of a temperature of at least 235° F. to portions of the foam material or film material to reduce the surface area of the portions of foam material or film material by at least 50 percent, based on the surface area of the opaque areas prior to the application of thermal energy, to less than about 0.15 square meters per gram.

31. The laminate material according to claim 28, wherein the opaque areas have surface areas of at least 0.5 square meters per gram, and the transparent areas have been formed by application of a temperature of at least 235° F. to portions of the foam material or film material to reduce the surface area of the portions of foam material or film material by at least 25 percent, based on the surface area of the opaque areas prior to the application of thermal energy, to less than about 0.375 square meters per gram.

32. The laminate material according to claim 28, wherein the transparent areas have been formed by application of a temperature of at least 235° F. to portions of the foam material or film material to reduce the surface area of the portions of foam material or film material by at least 40 percent, based on the surface area of the opaque areas prior to the application of thermal energy, to less than about 0.3 square meters per gram.

33. The laminate material according to claim 28, wherein the transparent areas have been formed by application of a temperature of at least 235° F. to portions of the foam material or film material to reduce the surface area of the portions of foam material or film material by at least 50 percent, based on the surface area of the opaque areas prior to the application of thermal energy, to less than about 0.25 square meters per gram.

34. The laminate material according to claim 28, wherein the opaque areas have surface areas of from about 0.6 to about 1.5 meters per gram, and the transparent areas have been formed by application of a temperature of at least 235° F. to portions of the foam material or film material to reduce the surface area of the portions of foam material or film material by at least 25 percent, based on the surface area of the opaque areas prior to the application of thermal energy, to less than about 1.125 square meters per gram.

35. The laminate material according to claim 28, wherein the transparent areas have been formed by application of a temperature of at least 235° F. to portions of the foam material or film material to reduce the surface area of the portions of foam material or film material by at least 40 percent, based on the surface area of the opaque areas prior to the application of thermal energy, to less than about 0.9 square meters per gram.

36. The laminate material according to claim 28, wherein the transparent areas have been formed by application of a temperature of at least 235° F. to portions of the foam material or film material to reduce the surface area of the portions of foam material or film material by at least 50 percent, based on the surface area of the opaque areas prior to the application of thermal energy, to less than about 0.75 square meters per gram.

37. A disposable absorbent garment, the garment comprising:
   a bodyside liner;
      an outer cover comprising a laminate material according to one of claims 2, 3, 5, 6, 8, 9, 11, 12, 14, 15, 17, 18, 20, 21, 23, 24, 26, 27, 29, 30, 32, 33, 35 or 36; and
   an absorbent core located between the bodyside liner and the outer cover.

38. A disposable absorbent garment, the garment comprising:
   a bodyside liner;
      an outer cover comprising a laminate material according to one of claims 2, 11, 20 or 29; and
   an absorbent core located between the bodyside liner and the outer cover;
      the disposable absorbent garment and outer cover comprising a laminate material being so configured that the transparent areas serve as wetness indicators, whereby a caretaker may visualize a color change indicating that the garment has been used.

39. A process of forming a laminate material according to one of claims 2, 3, 5, 6, 8, 9, 11, 12, 14, 15, 17, or 18, comprising:
   (1) forming a first layer of nonwoven fibrous material, the material having fibrous opaque areas and a coloration, the first layer having a basis weight of from about 5.0 to about 100 grams per square meter and being formed from fibrous material having a denier of less than about 2.0 d,
      wherein the opaque areas have surface areas of at least 0.3 square meters per gram and light transmissions of not more than about 40 percent;
   (2) applying a temperature of at least 230° F. to portions of the nonwoven material to reduce the surface area of the portions of nonwoven material by at least 25 percent, based on the surface area of the opaque areas prior to the application of thermal energy, to less than about 0.225 square meters per gram, to form transparent areas have light transmissions of greater than 80 percent; and
   (3) bonding a second layer of material to the first layer of material, the second layer of material having a different coloration than the first layer of material,
   whereby the coloration of the second layer of material is visible through the transparent areas of the first layer of material to a greater extent than through the opaque areas of the first layer of material.

40. A process of forming a laminate material according to one of claims 20, 21, 23, 24, 26, 27, 29, 30, 32, 33, 35, or 36, comprising:
   (1) forming a first layer of open or closed cell foam material or film material, the material having opaque areas and a coloration,
      the first layer having a basis weight of from about 5.0 to about 100 grams per square meter,
      wherein the opaque areas have surface areas of at least 0.3 square meters per gram and light transmissions of not more than about 40 percent;
   (2) applying a temperature of at least 235° F. to portions of the foam material or film material to reduce the surface area of the portions of foam material or film material by at least 25 percent, based on the surface area of the opaque areas prior to the application of thermal energy, to less than about 0.225 square meters per gram, to form transparent areas have light transmissions of greater than 80 percent; and
   (3) bonding a second layer of material to the first layer of material, the second layer of material having a different coloration than the first layer of material,
   whereby the coloration of the second layer of material is visible through the transparent areas of the first layer of material to a greater extent than through the opaque areas of the first layer of material.

* * * * *